(12) United States Patent
Brun et al.

(10) Patent No.: US 7,682,405 B2
(45) Date of Patent: *Mar. 23, 2010

(54) COLORING COMPOSITION COMPRISING AT LEAST ONE PIGMENT AND AT LEAST ONE ELECTROPHILIC CYANOACRYLATE MONOMER

(75) Inventors: Gaëlle Brun, Paris (FR); Luc Gourlaouen, Asnières (FR); Gabin Vic, Semoy (FR); Grégory Plos, Paris (FR); Aude Livoreil, Paris (FR); Franck Giroud, Chamoux sur Gelon (FR); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/200,180

(22) Filed: Aug. 28, 2008

(65) Prior Publication Data

US 2009/0193595 A1 Aug. 6, 2009

Related U.S. Application Data

(63) Continuation of application No. 11/248,317, filed on Oct. 13, 2005, now abandoned.

(60) Provisional application No. 60/638,110, filed on Dec. 23, 2004.

(30) Foreign Application Priority Data

Oct. 13, 2004 (FR) .................. 04 10800

(51) Int. Cl.
*A61Q 5/10* (2006.01)
(52) U.S. Cl. .................. 8/405; 8/552; 8/557; 8/558; 8/637.1; 132/202; 132/208
(58) Field of Classification Search ............ 8/405, 8/552, 557, 558, 637.1; 132/202, 208
See application file for complete search history.

(56) References Cited

U.S. PATENT DOCUMENTS

| | | | |
|---|---|---|---|
| 2,748,050 A | 5/1956 | Shearer et al. | |
| 3,518,762 A | 7/1970 | Takeuchi | |
| 3,527,224 A | 9/1970 | Rabinowitz | |
| 3,583,408 A | 6/1971 | Wall | |
| 3,591,767 A | 7/1971 | Mudie | |
| 3,615,972 A | 10/1971 | Morehouse, Jr. et al. | |
| 3,634,022 A | 1/1972 | Robbins et al. | |
| 3,663,501 A | 5/1972 | Adams et al. | |
| 3,667,472 A | 6/1972 | Halpern | |
| 3,699,076 A | 10/1972 | Thomsen et al. | |
| 3,840,490 A | 10/1974 | Gadzala et al. | |
| 3,995,641 A | 12/1976 | Kronenthal et al. | |
| 4,035,334 A | 7/1977 | Davydov et al. | |
| 4,180,913 A | 1/1980 | Takeuchi et al. | |
| 4,578,266 A | 3/1986 | Tietjen et al. | |
| 4,626,428 A | 12/1986 | Weisberg et al. | |
| 4,650,826 A | 3/1987 | Waniczek et al. | |
| 4,980,086 A | 12/1990 | Hiraiwa et al. | |
| 5,290,825 A | 3/1994 | Lazar | |
| 5,362,486 A | 11/1994 | Nandagiri et al. | |
| 5,645,609 A | 7/1997 | Andrean et al. | |
| 5,866,106 A | 2/1999 | Papay | |
| 5,990,479 A | 11/1999 | Weiss et al. | |
| 5,998,472 A | 12/1999 | Berger et al. | |
| 6,001,345 A | 12/1999 | Askill et al. | |
| 6,037,366 A | 3/2000 | Krall et al. | |
| 6,106,577 A * | 8/2000 | Audousset et al. ............. 8/403 |
| 6,207,193 B1 | 3/2001 | Pellegrini | |
| 6,224,622 B1 | 5/2001 | Kotzev | |
| 6,225,198 B1 | 5/2001 | Alivisatos et al. | |
| 6,274,127 B1 | 8/2001 | Schraer et al. | |
| 6,346,234 B1 | 2/2002 | Rollat et al. | |
| 6,620,846 B1 | 9/2003 | Jonn et al. | |
| 6,793,913 B2 | 9/2004 | Tournilhac et al. | |
| 7,186,274 B2 | 3/2007 | Vic et al. | |
| 7,357,921 B2 | 4/2008 | Giroud | |
| 2002/0034486 A1 | 3/2002 | Midha et al. | |
| 2002/0037310 A1 | 3/2002 | Jonn et al. | |
| 2003/0161804 A1 | 8/2003 | Perron et al. | |
| 2003/0175229 A1* | 9/2003 | Giroud ................... 424/70.12 |
| 2004/0001798 A1 | 1/2004 | Perron et al. | |
| 2004/0033206 A1 | 2/2004 | Dubief et al. | |
| 2004/0042993 A1 | 3/2004 | Gabin | |
| 2004/0156800 A1 | 8/2004 | Brun et al. | |
| 2004/0253757 A1 | 12/2004 | Gourlaouen | |
| 2006/0088493 A1 | 4/2006 | Vic et al. | |
| 2007/0231940 A1 | 10/2007 | Gourlaouen | |

FOREIGN PATENT DOCUMENTS

DE 199 01 484 7/2000

(Continued)

OTHER PUBLICATIONS

English Language Abstract for FR 1 511 320, (1968).

(Continued)

*Primary Examiner*—Eisa B Elhilo
(74) *Attorney, Agent, or Firm*—Finnegan, Henderson, Farabow, Garrett & Dunner L.L.P.

(57) ABSTRACT

The present disclosure relates to a dyeing composition comprising, in an appropriate dyeing medium, at least one pigment and at least one electrophilic cyanoacrylate monomer of formula (I)

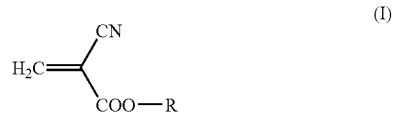

in which R is chosen from alkyl radicals and alkoxyalkyl radicals. Dyeing kits comprising said compositions and processes using same are also disclosed.

28 Claims, No Drawings

FOREIGN PATENT DOCUMENTS

| | | |
|---|---|---|
| DE | 199 55 842 | 6/2001 |
| EP | 0 056 219 | 7/1982 |
| EP | 0 112 807 | 7/1984 |
| EP | 0 320 473 | 6/1989 |
| EP | 0 348 372 | 12/1989 |
| EP | 0 486 080 | 5/1992 |
| EP | 0 512 243 | 11/1992 |
| EP | 1 064 918 | 1/2001 |
| EP | 1 184 426 A2 | 3/2002 |
| EP | 1 371 354 | 12/2003 |
| EP | 1 378 233 | 1/2004 |
| EP | 1 440 681 | 7/2004 |
| EP | 1 647 265 | 4/2006 |
| FR | 1 511 320 | 1/1968 |
| FR | 1 546 631 | 11/1968 |
| FR | 2 679 771 | 2/1993 |
| FR | 2 741 530 | 5/1997 |
| FR | 2 833 489 | 6/2003 |
| FR | 2 833 959 | 6/2003 |
| FR | 2 833 960 | 6/2003 |
| FR | 2 838 052 | 10/2003 |
| FR | 2 840 208 | 12/2003 |
| FR | 2 853 531 | 10/2004 |
| JP | 62100567 | 5/1987 |
| JP | 6-25613 | 2/1994 |
| JP | 2003-534406 | 11/2003 |
| WO | WO 98/38969 | 9/1998 |
| WO | WO 00/45777 | 8/2000 |
| WO | WO 0209785 A1 | 2/2002 |
| WO | WO 03053380 A2 | 7/2003 |
| WO | WO 2004/043330 | 5/2004 |

OTHER PUBLICATIONS

Dabboussi B.O. et al.: "(CdSe)ZnS Core-shell Quantum Dots: Synthesis and Characterisation of a Size Series of Highly Luminescent Nanocrystallites," Journal of Physical Chemistry B, vol. 101, 1997, pp. 9463-9475.
Peng, Xiaogang et al., "Epitaxial Growth of Highly Luminescent CdSe/CdS Core/Shell Nanocrystals with Photostability and Electronic Accessibility," Journal of the American Chemical Society, vol. 119, No. 30, pp. 7019-7029.
Jerry March: "Advanced Organic Chemistry," 3rd ed., pp. 141 & 151-161, (1985).
C. Zviak: "Science des Traitements Capillaires," Ed. Masson 1988, p. 278.
French Search Report for 04/10800 (the French Priority Application for U.S. Appl. No. 11/248,317, the present application).
STIC Search Report dated Jun. 8, 2007 (cited in Office Action dated Nov. 6, 2007 for parent U.S. Appl. No. 11/248,317), (2005).
Bachrach, A. et al., "Anionic Oligomerization of Dimethyl Itaconate," European Polymer Journal 12: pp. 563-569 (1976).
Bonner, B. et al. "The Polymerization of 3-methyl-N-(phenylsulfonyl)-1-aza-1,3-butadiene)," Polymer Bulletin 28: pp. 517-523 (1992).
Boor, J. et al. "Polymerization of Phenyl and Methyl Vinyl Sulfones with Anionic-Type Initiators," Polymer Science 9(1): 249-252 (1971).
Breton, P. et al. "Physico-Chemical Characterization, Preparation and Performance of Poly(methylidene malonate 2.1.2) Nanoparticles," Biomaterials 19: pp. 271-281 (1998).
Brinker, C.J., et al., "Sol Gel Science: The Physics and Chemistry of Sol-Gel Processing," published by Academic Press (ISBN 0-12-134970-5) (1990).
Chen, J. et al., "Solution Properties of Single Walled Carbon Nanotube," Science 282(2):pp. 95-98 (1998).
Copending U.S. Appl. No. 11/248,286, filed Oct. 13, 2005.
Copending U.S. Appl. No. 11/248,335, filed Oct. 13, 2005.
Copending U.S. Appl. No. 11/393,738, filed Mar. 31, 2006.
Copending U.S. Appl. No. 11/544,576, filed Oct. 10, 2006.
Copending U.S. Appl. No. 11/783,928, filed Apr. 13, 2007.
Copending U.S. Appl. No. 11/784,000, filed Apr. 13, 2007.
Copending U.S. Appl. No. 11/785,005, filed Apr. 13, 2007.
De Keyser, J-L et al., "Poly(diethyl methyldenemalonate) Nanoparticles as a Potential Drug Carrier: Preparation, Distribution, and Elimination after intravenous and Peroral Administration to Mice," J. Pharm. Sci. 80(1): pp. 67-70 (1991).
English language Abstract of DE 199 01 484, dated Jul. 20, 2000.
English language Abstract of DE 199 55 842, dated Jun. 7, 2001.
English language Abstract of EP 1 064 918, dated Jan. 3, 2001.
English language Abstract of EP 1 371 354, dated Dec. 17, 2003.
English language Abstract of EP 1 378 233, dated Jan. 7, 2004.
English language Abstract of FR 1 546 631, dated Nov. 22, 1968.
English language Abstract of FR 2 853 531, dated Oct. 15, 2004.
English language Abstract of JP 2003-534406, dated Nov. 18, 2003.
English language Abstract of JP 6-25613, dated Feb. 1, 1994.
English language Abstract of WO 00/45777, dated Aug. 10, 2000.
European Examination Report for EP 05 29 2145, dated Jan. 6, 2006 (related to Copending U.S. Appl. No. 11/248,286).
European Search Report for EP 05 29 2145, dated Jan. 19, 2006, (related to Copending U.S. Appl. No. 11/248,286).
French Search Report for FR 04/10813, dated Jun. 6, 2005, for Copending U.S. Appl. No. 11/248,335.
French Search Report for FR 05/03152, dated Nov. 14, 2005.
French Search Report for FR 05/53061, dated Jul. 19, 2006, (related to Copending U.S. Appl. No. 11/544,576).
French Search Report for FR 06/03281, dated Jan. 11, 2007.
French Search Report for FR 06/03284, dated Feb. 2, 2007.
French Search Report for FR 06/03286, dated Dec. 20, 2006, (related to Copending U.S. Appl. No. 11/785,004).
Fu, Q. et al., "Selective Coating of Single Wall Carbon Nanotubes with Thin $SiO_2$ Layer," Nano. Lett. 2(4): pp. 329-332 (2002).
Georgakilas, V. et al, "Organic Functionalization of Carbon Nanotubes," J. Am. Soc. 124(5): pp. 760-761 (2002).
Gipstein, E. et al., "Synthesis and Polymerization of Alkyl a-(Alkylsulfonyl)acrylates," J. Org. Chem. 45: 1486-89 (1980).
Hamon, M.A. et al., "Dissolution of Single-Walled Carbon Nanotubes," Adv. Mater. 11(10): pp. 834-40 (1999).
Han, M. et al., "Quantum-Dot-Tagged Microbeads for Multiplexed Optical Coding of Biomolecules," Nature Biotechnology, 19: pp. 631-635 (2001).
Holzinger, M. et al., "A New Purification Method for Single-Walled Carbon Nanotubes (SWNTs)," Appl. Phys. A 70: pp. 599-602 (2000).
Holzinger, M. et al., "Exohedral Sidewall reactions of Single Walled Carbon Nanotubes," Proceeding of the XV International Winter School: Electronic Properties of Molecular Nanostructures, Kirchberg, Austria, Mar. 2001, pp. 337-340.
Hopff, V.H. et al., "Uber die Polymerisation des Methylenmalonsaurediathylesters," Makromoleculare Chemie, pp. 95-106 (1961).
Huang, W. et al., "Sonication-Assisted Functionalization and Solubilization of Carbon Nanotubes," Nano. Lett. 2(3): pp. 231-234 (2002).
Ishizone, T. et al., "Controlled Anionic Polymerization of tert-Butyl Acrylate with Diphenylmethylpotassium in the Presence of Triethylborane," Macromolecules 32: pp. 955-57 (1999).
John, G. et al., "Nanotube Formation from Renewable Resources via Coiled Nanofibers," Adv. Mat. 13(10): pp. 715-718 (2001).
Kanga, R. et al., "Anionic Polymerization and Copolymerization of Phenyl Vinyl Sulfoxide and Thermal Degradation Studies of Poly(phenylvinylsulfoxide)," Polymer Preprints (ACS, Division of Polymer Chemistry) pp. 322-323 (1987).
Klemarczyk, P. "A General Synthesis of 1,1 Disubstituted Electron Deficient Olefins and their Polymer Properties," Polymer 39(1): pp. 173-181 (1998).
Kobayashi, M. et al., "Anionic Polymerization of N,N-Dialkylacrylamides Containing Alkoxysilyl Groups in the Presence of Lewis Acids," Journal of Polymer Science, Part A: Polymer Chemistry 43: pp. 2754-2764 (2005).
Kudin, K.N. et al., "Fluorinated Single-Wall Carbon Nanotubes," Phys. Rev. B63-045413-1, 045413-8 (2001).
Lescure, F. et al., "Preparation and Characterization of Novel Poly(methylidene Malonate 2.1.2.)-Made Nanoparticles," Pharmaceutical Research 11: pp. 1270-1277 (1994).

Masuda, M. et al., Polymerization in Nanometer-Sized Fibers: Molecular Packing Order and Polymerizability, Macromol3ecules 33: pp. 9233-9238 (2000).

Mittal, J. et al., "Room Temperature Filling of Single-Wall Carbon Nanotubes with Chromium Oxide in Open Air," Chem. Phys. Lett. 339: pp. 311-318 (2001).

Office Action mailed Mar. 31, 2008, in co-pending U.S. Appl. No. 11/248,286.

Office Action mailed Oct. 15, 2008, in co-pending U.S. Appl. No. 11/248,286.

Office Action mailed Jul. 20, 2009, in co-pending U.S. Appl. No. 11/248,286.

Office Action mailed Mar. 4, 2009, in co-pending U.S. Appl. No. 11/248,335.

Office Action mailed Jul. 15, 2008, in co-pending U.S. Appl. No. 11/544,576.

Office Action mailed Mar. 19, 2009, in co-pending U.S. Appl. No. 11/544,576.

Pompeo, F. et al, "Water Solubilization of Single-Walled Carbon Nanotubes by Functionalization with Glucosamine," Nano. Lett. 2(4): pp. 369-373 (2002).

Rozenberg, B. "Proton-Transfer Anionic Polymerization of Vinyl Monomers," International Journal of Plastics technology, vol. 6: pp. 17-21 (2003).

Sayyah, S.M. etal., "Characterization and Gamma Radiation Effects on Poly(methyl methacrylate) Doped with Some Benzyliden Polymers," J. polym Res. 7(2): pp. 97-106 (2000).

Schlossman, M. et al., "Treated Pigments, New Ways to Impart Color on the Skin," Cosmetics & Toiletries, vol. 105, pp. 53-64 (1990).

Schmitt, B. et al., "Anionic Polymerization of (Meth)acrylates in the Presence of Tetraalkylammonium Halide-Trialkyl Aluminum Complexes in Toluene. 3. Kinetic Investigations on Primary Acrylates," Macromolecules 34: pp. 2115-2120 (2001).

Shimizu, T., "Bottom-Up Synthesis and Structural Properties of Self-Assembled High-Axial-Ratio Nanostructures," Macromol. Rapid Commun. 23(5/6): pp. 311-331 (2002).

Watanabe, H. et al. "Polymerization of N-alkyl-substituted Itaconimides and N-(alkyl-substituted phenyl) Itaconimides and Characterization of the Resulting Polymers," J. Polymer Science: Part A: Polymer Chemistry 32: pp. 2073-2083 (1994).

Wells, P.R., "Group Electronegativities," Progress in Phys. Org. Chem., vol. 6: pp. 111-145 (1968).

Office Action mailed Nov. 17, 2009, in co-pending U.S. Appl. No. 11/248,335.

* cited by examiner

COLORING COMPOSITION COMPRISING AT LEAST ONE PIGMENT AND AT LEAST ONE ELECTROPHILIC CYANOACRYLATE MONOMER

This is a continuation of U.S. application Ser. No. 11/248,317, filed Oct. 13, 2005, now abandoned which claims right to priority under 35 U.S.C. §119 based on French Patent Application No. 0410800, filed Oct. 13, 2004, and which claims the benefit of U.S. Provisional Application No. 60/638,110, filed Dec. 23, 2004, all of which are incorporated herein by reference.

This application claims benefit of U.S. Provisional Application No. 60/638,110 filed Dec. 23, 2004, the contents of which are incorporated herein by reference. This application also claims benefit of priority under 35 U.S.C. §119 to French Patent Application No. 04 10800, filed Oct. 13, 2004, the contents of which are also incorporated by reference.

The present disclosure relates to a composition for coloring/dyeing keratin materials, for instance keratin fibers such as the hair, comprising at least one pigment and at least one particular electrophilic monomer, and a process for dyeing keratin materials using this composition.

Within the field of coloring keratin fibers it is already known to color keratin fibers by a variety of techniques, starting from direct dyes or pigments, for non-permanent colorations, or from dye precursors, for permanent colorations.

Non-permanent coloration or direct coloration involves dyeing the keratin fibers with dyeing compositions containing direct dyes. These dyes are colored, and coloring molecules which have an affinity for the keratin fibers. They are applied to the keratin fibers for a time required for the desired coloration to be obtained, then rinsed off.

The conventional dyes which are used include, for example, dyes of the nitrobenzene, anthraquinone, nitropyridine, azo, xanthene, acridine, azine or triarylmethane type or natural dyes.

Some of these dyes can be used under lightening conditions, allowing colorations to be obtained which are visible on dark hair.

It is also known to dye keratin fibers permanently by oxidation coloring. This coloring technique involves applying to the keratin fibers a composition containing dye precursors such as oxidation bases and couplers. These precursors, under the action of an oxidant, will form at least one colored species in the hair.

The variety of molecules employed as oxidation bases and couplers can make it possible to obtain a rich palette of colors, and the colorations resulting from them can be permanent, powerful, and/or resistant to external agents, in particular to light, inclement weather, washing, perspiration, and rubbing.

In order to be visible on dark hair, the colorations resulting from these two coloring techniques require a prior or simultaneous bleaching of the keratin fibers. This bleaching step, carried out with an oxidant such as hydrogen peroxide or persalts, can entail a not inconsiderable amount of degradation of the keratin fibers, which may impair their cosmetic properties. The hair then has a tendency to become rough, less easy to disentangle, and/or more fragile.

Another method of coloring keratin fibers involves using pigments. In effect, the use of a pigment at the surface of the keratin fibers makes it possible, generally speaking, to obtain colorations which are visible on dark hair, since the surface pigment masks the natural color of the fiber. The use of pigments for coloring keratin fibers is described, for example, in French Patent Application Publication No. FR 2 741 530, which recommends the use, for the coloring of the keratin fibers, of a composition comprising at least one dispersion of particles of film-forming polymer comprising at least one acid functional group, and at least one pigment dispersed in the continuous phase of said dispersion.

The coloration obtained by this mode of coloring can have the drawback of having a low level of resistance to shampooing.

French Patent Application Publication No. FR 2 833 489 discloses hair treatment compositions on the basis of compositions comprising electrophilic monomers. A composition of this kind can make it possible to obtain hair which is extremely well coated and not greasy.

The present disclosure, therefore, relates to new compositions for coloring or dyeing keratin materials, for instance keratin fibers such as the hair, which make it possible to obtain colorations which are visible on dark hair, without the need to lighten or bleach the fibers, and/or which may exhibit good resistance to shampooing.

Thus, in one embodiment, the present disclosure relates to a process for dyeing keratin materials such as keratin fibers comprising applying to the fibers a dyeing composition comprising, in a suitable dyeing medium, at least one pigment and at least one electrophilic cyanoacrylate monomer of formula (I)

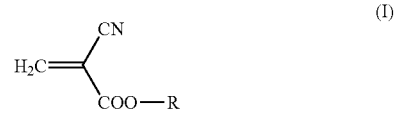

in which R is chosen from alkyl radicals and alkoxyalkyl radicals.

The present disclosure also relates to a composition comprising, in a suitable dyeing medium, at least one pigment in an amount greater than 5% (w/w) by weight and at least one cyanoacrylate electrophilic monomer of formula (I).

The process in accordance with the present disclosure can make it possible to obtain a visible coloration on a dark keratin material. For example, in the case of dark keratin fibers, a highly visible coloration is obtained with no need to lighten or bleach the keratin fibers and hence it is possible to obtain a visible coloration on a dark keratin material without risking physical degradation of the keratin fibers. Moreover, this coloration exhibits good resistance to the various aggressive influences to which the hair may be subjected, such as shampooing, rubbing, light, inclement weather, perspiration, and permanent reshaping ("perming"). In at least one embodiment, the coloration shows good resistance to shampooing.

Given the variety of pigments which can be used in the composition of the present disclosure, it is possible to obtain colorations in varied, powerful and aesthetic shades, which can also be chromatic.

The present disclosure additionally relates to a kit comprising compositions comprising at least one pigment and at least one electrophilic cyanoacrylate monomer of formula (I).

As used herein, a "pigment" is understood to mean any organic and/or inorganic entity whose solubility in water is less than 0.01% at 20° C., for instance less than 0.0001%, and which exhibits absorption at a wavelength ranging from 350 nm to 700 nm, such as absorption with one maximum.

The pigments that can be useful in the present disclosure are selected from any organic and/or inorganic pigments known in the art, such as those described in the Kirk-Othmer encyclopaedia of chemical technology and in the Ullmann encyclopaedia of industrial chemistry.

The at least one pigment may be present in pigment paste or powder form.

The at least one pigment in accordance with the present disclosure may, for example, be chosen from white and/or colored pigments, lakes, special-effect pigments such as nacres or flakes, and mixtures thereof.

Non-limiting examples of white or colored inorganic pigments include titanium dioxide, with or without surface treatment, oxides of zirconium or of cerium, oxides of iron or of chromium, manganese violet, ultramarine blue, chromium hydrate and Prussian Blue. For example, the following inorganic pigments may be used: $Ta_2O_5$, $Ti_3O_5$, $Ti_2O_3$, TiO, $ZrO_2$ mixed with $TiO_2$, $ZrO_2$, $Nb_2O_5$, $CeO_2$, ZnS.

Non-limiting examples of white or colored organic pigments include nitroso, nitro, azo, xanthene, quinoline, anthraquinone and phthalocyanine compounds, metal complex compounds, and isoindolinone, isoindoline, quinacridone, perinone, perylene, diketopyrrolopyrrole, thioindigo, dioxazine, triphenylmethane and quinophthalone compounds.

For instance, by way of non-limiting example, the white or colored organic pigments may be chosen from carmine, carbon black, aniline black, azo yellow, quinacridone, phthalocyanine blue, sorghum red, the blue pigments codified in the Colour Index under references CI 42090, 69800, 69825, 73000, 74100 and 74160, the yellow pigments codified in the Colour Index under references CI 11680, 11710, 15985, 19140, 20040, 21100, 21108, 47000 and 47005, the green pigments codified in the Colour Index under references CI 61565, 61570, 74260, the orange pigments codified in the Colour Index under references CI 11725, 15510, 45370 and 71105, the red pigments codified in the Colour Index under references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, pigments obtained by oxidative polymerization of indole or phenolic derivatives as described in French Patent No. FR 2 679 771.

It is also possible to use pigment pastes of organic pigment, such as the products sold by the company Hoechst under the name:

Jaune Cosmenyl IOG: Pigment Yellow 3 (CI 11710);
Jaune Cosmenyl G: Pigment Yellow 1 (CI 11680);
Orange Cosmenyl GR: Pigment Orange 43 (CI 71105);
Rouge Cosmenyl R: Pigment Red 4 (CI 12085);
Carmin Cosmenyl FB: Pigment Red 5 (CI 12490);
Violet Cosmenyl RL: Pigment Violet 23 (CI 51319);
Bleu Cosmenyl A2R: Pigment Blue 15.1 (CI 74160);
Vert Cosmenyl GG: Pigment Green 7 (CI 74260);
Noir Cosmenyl R: Pigment Black 7 (CI 77266).

The pigments in accordance with the present disclosure may also be in the form of composite pigments as described in European Patent No. EP 1 184 426. These composite pigments may be composed of, for example, particles comprising an inorganic core, at least one binder attaching the organic pigments on the core, and at least one organic pigment at least partly covering the core.

As used herein, the term "lakes" is understood to mean dyes adsorbed on insoluble particles, the resultant assembly remaining insoluble during use. The inorganic substrates on which the dyes are adsorbed are, for example, alumina, silica, calcium sodium borosilicate or calcium aluminium borosilicate, and aluminium. Among the organic dyes, non-limiting mention may be made of cochineal carmine.

Non-limiting examples of lakes include the products known under the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 7 (CI 15 850:1), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 1 O (CI 77 002), D & C Green 3 (CI 42 053) and D & C Blue 1 (CI 42 090).

As used herein, the term "special-effect pigments" is understood to mean pigments which create, generally speaking, a colored appearance (characterized by a certain shade, a certain liveliness and a certain lightness) which is not uniform and which changes as a function of the conditions of observation (e.g., light, temperature, viewing angles, etc.). They are consequently in contrast to white or colored pigments, which provide a conventional opaque, semi-transparent or transparent, uniform hue.

Non-limiting examples of special-effect pigments include white nacreous pigments such as mica coated with titanium or with bismuth oxychloride, colored nacreous pigments such as mica coated with titanium and iron oxides, mica coated with titanium, and, for instance, Prussian Blue or chromium oxide, mica coated with titanium and an organic pigment as defined above, and also nacreous pigments based on bismuth oxychloride. Nacreous pigments include the nacres Cellini, sold by Engelhard (mica-$TiO_2$-lake), Prestige, sold by Eckart (mica-$TiO_2$) and Colorona, sold by Merck (mica-$TiO_2$—$Fe_2O_3$).

Non-limiting mention may also be made of interference-effect pigments not attached to a substrate, such as liquid crystals (Helicones HC from Wacker), holographic interference flakes (Geometric Pigments or Spectra f/x from Spectratek). Special-effect pigments can also comprise fluorescent pigments, whether they be daylight-fluorescent substances or substances which produce ultraviolet fluorescence, phosphorescent pigments, photochromic pigments, thermochromic pigments, and quantum dots, sold for example by the company Quantum Dots Corporation.

The quantum dots are luminescent semi-conductive nanoparticles capable of emitting, under excitation by light, radiation having a wavelength ranging from 400 nm to 700 nm. These nanoparticles are known from the literature. For instance, they may be manufactured by the processes described, for example, in U.S. Pat. No. 6,225,198 or 5,990,479, in the publications cited therein, and also in the following publications: Dabboussi B. O. et al "*(CdSe)ZnS Core-shell Quantum Dots: Synthesis and Characterisation of a Size Series of Highly Luminescent Nanocrystallites*" Journal of Physical Chemistry B, Vol. 101, 1997, pp 9463-9475, and Peng, Xiaogang et al, "*Epitaxial Growth of Highly Luminescent CdSe/CdS core/shell nanocrystals with Photostability and Electronic Accessibility*," Journal of the American Chemical Society, Vol. 119, No. 30, pp 7019-7029.

The variety of pigments which can be used in the present disclosure allows a rich palette of colors to be obtained, and also certain optical effects, such as metallic and interference effects.

According to one embodiment of the present disclosure, the at least one pigment is chosen from colored pigments. As used herein, the term "colored pigments" is understood to mean pigments other than the white pigments.

The size of the at least one pigment which can be used in the context of the present disclosure can range from 10 nm to 200 μm, for instance, from 20 nm to 80 μm, and such as from 30 nm to 50 μm.

The at least one pigment can be present in the composition in accordance with the present disclosure, in an amount for each pigment, ranging from 0.05% to 50% by weight, relative to the total weight of the composition, such as ranging from 0.1% to 35% by weight, relative to the total weight of the composition.

In the context of the present disclosure, the alkyl or alkoxyalkyl radicals may be linear or branched, and may be cyclic.

Non-limiting examples of cyanoacrylate monomers of formula (I) include the electrophilic monomers ethyl 2-cyanoacrylate, methyl 2-cyanoacrylate, n-propyl 2-cyanoacrylate, isopropyl 2-cyanoacrylate, tert-butyl 2-cyanoacrylate, n-butyl 2-cyanoacrylate, isobutyl 2-cyanoacrylate, 3-methoxybutyl cyanoacrylate, n-decyl cyanoacrylate, hexyl 2-cyanoacrylate, 2-ethoxyethyl 2-cyanoacrylate, 2-methoxyethyl 2-cyanoacrylate, 2-octyl 2-cyanoacrylate, 2-propoxyethyl 2-cyanoacrylate, n-octyl 2-cyanoacrylate and isoamyl cyanoacrylate.

According to one embodiment of the present disclosure, the at least one electrophilic cyanoacrylate monomer of formula (I) is chosen from those comprising alkyl or alkoxyalkyl radicals R of 1 to 10 carbon atoms, such as of 6 to 10 carbon atoms.

According to another embodiment of the present disclosure, the at least one electrophilic cyanoacrylate monomer is chosen from alkyl($C_6$-$C_{10}$)cyanoacrylates. According to still another embodiment, the at least one electrophilic cyanoacrylate monomer is chosen from octyl 2-cyanoacrylate monomers, linear or branched.

In yet another embodiment of the present disclosure, the at least one electrophilic cyanoacrylate monomer is chosen from those of the following formula and mixtures thereof:

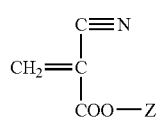

(F)

in which: Z is chosen from —$(CH_2)_7$—$CH_3$, $CH(CH_3)$—$(CH_2)_5$—$CH_3$, $CH_2$—$CH(C_2H_5)$—$(CH_2)_3$—$CH_3$, $(CH_2)_5$—$CH(CH_3)$—$CH_3$, and $(CH_2)_4$—$CH(C_2H_5)$—$CH_3$ monomers.

The at least one electrophilic cyanoacrylate monomer used in the composition of the present disclosure may be attached covalently to supports such as polymers, oligomers or dendrimers. The polymer or oligomer may have a linear, branched, comb or block structure. The distribution of the monomers of the present disclosure over the polymeric, oligomeric or dendritic structure may be random, terminal or blockwise.

In the composition of the present disclosure, the at least one electrophilic cyanoacrylate monomer can be present in an amount ranging from 0.1% to 80% by weight, relative to the total weight of the composition, such as from 1% and 50%.

In the context of the present disclosure, the electrophilic cyanoacrylate monomers of formula (I) are monomers capable of undergoing anionic polymerization in the presence of an nucleophile. As used herein, the term "anionic polymerization" is understood to mean the mechanism defined in the work "Advanced Organic Chemistry," third edition, by Jerry March, pages 151 to 161. The nucleophiles capable of initiating the anionic polymerization are systems which are known per se and which are capable of generating a carbanion on contact with a nucleophile, such as the hydroxide ions present in water at neutral pH. As used herein, the term "carbanions" is understood to mean the chemical species defined in "Advanced Organic Chemistry," third edition, by Jerry March, page 141.

The nucleophiles may be applied independently of the composition of the present disclosure. They may also be added to the composition of the present disclosure at the time of use.

The nucleophile is a molecular compound, an oligomer, a dendrimer or a polymer which possesses nucleophilic functional groups. Without limitation, nucleophilic functional groups that may be mentioned include the following functional groups: $R_2N^-$, $NH_2^-$, $Ph_3C^-$, $R_3C^-$, $PhNH^-$, pyridine, $ArS^-$, $R$—$C\equiv C^-$, $RS^-$, $SH^-$, $RO^-$, $R_2NH$, $ArO^-$, $N_3^-$, $OH^-$, $ArNH_2$, $NH_3$, $I^-$, $Br^-$, $Cl^-$, $RCOO^-$, $SCN^-$, $ROH$, $RSH$, $NCO^-$, $CN^-$, $NO_3$, $ClO_4^-$ and $H_2O$, wherein Ph is a phenyl group; Ar is an aryl group, and R is a $C_1$-$C_{10}$ alkyl group.

The at least one electrophilic cyanoacrylate monomer of formula (I) according to the present disclosure may be synthesized by the known methods described in the art. For example, the electrophilic cyanoacrylate monomers may be synthesized according to the teaching of U.S. Pat. Nos. 3,527,224, 3,591,767, 3,667,472, 3,995,641, 4,035,334 and 4,650,826.

The suitable dyeing medium used in the composition of the present disclosure can be, for example, a non-hygroscopic anhydrous medium. As used herein, the term "anhydrous medium" is understood to mean a medium comprising less than 1% of water by weight.

According to one embodiment the dyeing medium of the composition of the present disclosure can be chosen, for example, from:
aromatic alcohols such as benzyl alcohol;
fatty alcohols;
modified and non-modified polyols, such as glycerol, glycol, propylene glycol, dipropylene glycol, butylene glycol and butyl diglycol;
volatile and non-volatile silicones, such as cyclopentasiloxane, cyclohexasiloxane, polydimethylsiloxanes with or without modification by phenyl and/or siloxy and/or silanol and/or amine and/or imine and/or fluoroalkyl and/or carboxyl and/or betaine and/or quaternary ammonium and/or etc. functions;
mineral oils, organic oils, vegetable oils;
oxyethylenated and non-oxyethylenated waxes, paraffins and alkanes, such as $C_5$ to $C_{10}$ alkanes;
fatty acids, fatty amides, fatty esters, and for instance fatty alcohol salicylates or benzoates.

According to one embodiment of the present disclosure, the medium is composed of a silicone, such as polydimethylsiloxanes and modified polydimethylsiloxanes.

The dyeing medium of the composition of the present disclosure may also be in the form of an emulsion and/or may be encapsulated, the at least one electrophilic monomer being maintained within an anhydrous medium until the moment of use. When the dyeing medium is an emulsion, this emulsion can comprise, for example, a disperse or continuous phase which may be composed of water, $C_1$-$C_4$ aliphatic alcohols or mixtures thereof, and an anhydrous organic phase comprising the at least one monomer. In the case of capsules or microcapsules, the capsules may comprise the at least one monomer in an anhydrous medium, and may themselves be dispersed in an anhydrous medium as defined above, water, $C_1$-$C_4$ aliphatic alcohols or mixtures thereof.

The organic compounds can be chosen from, for example, compounds which are liquid at a temperature of 25° C. and under 105 Pa (760 mmHg).

It is also possible to introduce at least one polymerization inhibitor into the composition of the present disclosure, such as free-radical and/or anionic polymerization inhibitors, in order to increase the stability of the composition over time. Without limitation, mention may be made of the following polymerization inhibitors: sulphur dioxide, nitric oxide, organic acids such as a sulphonic acid or phosphoric acid, acetic acid, lactone, boron trifluoride, hydroquinone and its derivatives such as hydroquinone monoethyl ether, tert-butylhydroquinone, benzoquinone and its derivatives such as duroquinone, catechol and its derivatives such as tert-butylcatechol and methoxycatechol, anisole and its derivatives such as methoxyanisole or hydroxyanisole, pyrogallol and its derivatives, p-methoxyphenol, hydroxybutyltoluene, alkyl sulphates, alkyl sulphites, alkyl sulphones, alkyl sulphoxides, alkyl sulphides, mercaptans, and mixtures thereof. The alkyl groups can be, for instance, chosen from groups having from 1 to 6 carbon atoms.

The at least one inhibitor can be present in the composition of the present disclosure in an amount ranging from 10 ppm to 10% by weight, such as from 50 ppm to 5% by weight, relative to the total weight of the composition.

The composition of the present disclosure may also comprise at least one polymer which does not exhibit any reactivity with the at least one electrophilic cyanoacrylate monomer, and which is capable of increasing the viscosity of the composition. The increase in viscosity can make it possible to reduce the polymerization rate of the cyanoacrylate monomers. In order to do this it is possible to add to the composition of the present disclosure, non-exhaustively, polymethyl methacrylate (PMMA) or else cyanoacrylate-based copolymers of the kind described in U.S. Pat. No. 6,224,622.

The composition of the present disclosure may also comprise at least one filler. As used herein, the term "filler" is understood to mean, without limitation, colorless or white, mineral or synthetic, lamellar or non-lamellar particles. The at least one filler may be present in an amount ranging from 0% to 48% by weight, relative to the total weight of the composition, for instance from 0.01% to 30% by weight, and such as from 0.02% to 20% by weight. Non-limiting mention may be made, for example, of talc, zinc stearate, mica, kaolin, polyamide (Nylon®) powders (ORGASOL from Atochem), polyethylene powders, tetrafluoroethylene polymer powders (Teflon®), starch, boron nitride, polymeric microspheres such as those of polyvinylidene chloride/acrylonitrile, for instance EXPANCEL (Nobel Industries), and of acrylic acid copolymers (Polytrape from the company Dow Corning) and silicone resin microbeads (Tospearls® from Toshiba, for example), and elastomeric organopolysiloxanes.

The composition may also comprise at least one conventional cosmetic adjuvant. Without limitation, mention may be made of reductants, oxidants, fats, silicones, thickeners, softeners, antifoams, moisturizers, emollients, alkalifiers, elastomers, plasticizers, sunscreens, clays, colloidal minerals, perfumes, peptizers, preservatives, anionic, cationic, amphoteric, zwitterionic or nonionic surfactants, fixative or non-fixative polymers, conditioning polymers, proteins, and vitamins.

The composition disclosed herein may also comprise at least one metal powder or particle, such as particles or powders of aluminium and of copper.

These compositions may be present in a variety of forms, such as lotions, sprays and mousses, and may be applied as a shampoo or conditioner.

In the case of sprays, the composition of the present disclosure may comprise at least one propellant. The propellant is composed of the compressed or liquefied gases which are commonly employed for preparing aerosol compositions. For example, the at least one propellant can be chosen from air, carbon dioxide, compressed nitrogen or else a soluble gas such as dimethyl ether, hydrocarbons which are halogenated (e.g., fluorinated) or non-halogenated, and mixtures thereof.

The present disclosure also relates to a process comprising applying the composition of the present disclosure to keratin materials, for instance keratin fibers such as the hair, in the presence of at least one nucleophile.

According to one embodiment of the process of the present disclosure, the at least one nucleophile capable of initiating the polymerization of the at least one cyanoacrylate monomer may be applied to the keratin fibers beforehand. The at least one nucleophile may be used in pure form, in solution, or in the form of an emulsion, or may be encapsulated. It may also be added to the anhydrous composition at the time of use, just before application to the keratin fibers.

By way of non-limiting example, the at least one nucleophile can be water. This water may be provided, for example, by prior wetting of the keratin fibers. It may also be added directly to the composition before application.

According to one embodiment, it is possible to modify the polymerization kinetics by wetting the fibers beforehand by means of an aqueous solution whose pH has been adjusted using a base, an acid or an acid/base mixture. The acid and/or the base may be inorganic or organic.

According to another embodiment, the process of the present disclosure may be carried out in a number of steps comprising applying a composition containing at least one pigment to the fibers, and then applying a composition comprising the at least one electrophilic cyanoacrylate monomer of formula (I), wherein the at least one nucleophile is present in the composition comprising the pigment or in a separate composition. According to this embodiment, the composition comprising the at least one pigment can be, for example, an aqueous solution of pigments, which allows the fiber to be wetted and the polymerization to be initiated when the at least one electrophilic cyanoacrylate monomer is applied.

According to the process of the present disclosure, another embodiment comprises either applying the at least one electrophilic cyanoacrylate monomer and the at least one pigment from a single composition, or applying the at least one pigment in a first phase and then the at least one electrophilic cyanoacrylate monomer.

The process of the present disclosure may include additional, intermediate or final, steps, such as the application of a cosmetic product, a rinsing step and/or a drying step. Drying may be carried out under a hood, with a hairdryer and/or with a smoothing iron. For example, the application of the compositions in accordance with the present disclosure may be followed by a rinsing operation.

It is also possible to carry out multiple applications of the composition of the present disclosure, so as to obtain a superposition of layers, to achieve specific properties of the deposit in terms of chemical nature, mechanical strength, thickness, appearance and/or feel.

In order to improve, among other things, the adhesion of the poly(cyanoacrylate) formed in situ, the fiber may be pretreated with any types of polymer.

In order to modify the anionic polymerization kinetics it is also possible to enhance the nucleophilicity of the fiber by chemical conversion of the keratin fibers. By way of example, non-limiting mention may be made of the reduction of the disulfide bridges, of which the keratin is partly composed, to thiols before the composition of the present disclosure is applied. Non-exhaustively, mention may be made, as reductants of the disulfide bridges of which the keratin is partly composed, of the following compounds: anhydrous sodium thiosulphate, powdered sodium metabisulphite, thiourea, ammonium sulphite, thioglycolic acid, thiolactic acid, ammonium thiolactate, glycerol monothioglycolate, ammonium thioglycolate, thioglycerol, 2,5-dihydroxybenzoic acid, diammonium dithioglycolate, strontium thioglycolate, calcium thioglycolate, zinc formaldehyde-sulphoxylate, isooctyl thioglycolate, dl-cysteine and monoethanolamine thioglycolate.

Application of the composition of the present disclosure may also be preceded by a hair treatment, such as a direct or oxidation coloring operation.

According to the present disclosure, the at least one electrophilic cyanoacrylate monomer can be chosen from, for example, monomers capable of undergoing polymerization on the keratin fibers under cosmetically acceptable conditions. For instance, the polymerization of the at least one electrophilic cyanoacrylate monomer can take place at a temperature less than or equal to 80° C., such as ranging from 10° C. to 80° C., for example ranging from 20° C. to 80° C., which does not prevent the application being finished by drying under a hood, blow-drying or the passage of a flat iron or curling tongs.

The present disclosure additionally relates to a coloring kit comprising at least one first composition, which comprises at least one pigment, and at least one second composition, which comprises at least one electrophilic cyanoacrylate monomer of formula (I) and, optionally, at least one third composition, which comprises at least one nucleophile. According to this embodiment, the at least one composition comprising the at least one pigment is an aqueous composition and the at least one composition comprising the at least one electrophilic cyanoacrylate monomer is an anhydrous composition.

According to another embodiment, the kit comprises at least one first, anhydrous composition, which comprises at one pigment and at least one electrophilic cyanoacrylate monomer, and at least one second composition, which comprises at least one nucleophile.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The non-limiting examples below make it possible to illustrate the present disclosure without, however, limiting its scope.

EXAMPLES

Tests were conducted using the following compounds:

Monomer: 2-octyl 2-cyanacrylate stabilized with 1% of phosphoric acid, known under the name Rite Lok CON895, sold by the Chemence company Pigment 1: Brown iron oxide CI 77491, sold by LCW, Pigment 2: Titanium oxide/mica nacre with gold interference glints, sold by Eckart under the name Prestige Gold.

Coloring/Dyeing Medium:

50% poly(alpha-omega-dihydroxydimethylsiloxane)/cyclopentadimethylsiloxane (14.7/85.3) mixture, sold by Dow Corning under the name DC 1501 Fluid 50% cyclopentadimethylsiloxane sold by Dow Corning under the name DC 245 Fluid.

Example 1

An aqueous composition was prepared with 10% by weight of pigment 1. 0.5 g of this aqueous solution was applied to 1 g of a lock of clean, dry natural hair with a tone height of 4, corresponding to a natural chestnut shade in accordance with the classification of natural shades that is described in "Science des Traitements Capillaires," by C. Zviak, Ed. Masson 1988, p. 278.

The lock was subsequently dried under a hood, then wetted with 0.5 g of water. Applied to this wetted lock was 0.5 g of a composition comprising the above-described coloring medium and 10% by weight of the cyanoacrylate monomer.

After an exposure time of 15 minutes, the lock was dried for 2 minutes with a hairdryer.

The lock obtained was colored orange and the color obtained lasted for at least six shampooings.

Example 2

A composition was prepared comprising 10% by weight of pigment 2 in the above-described coloring medium. The cyanoacrylate monomer was added to this composition to give a final monomer concentration of 10% by weight. 0.5 g of this composition was applied to a lock of clean, dry natural hair with a tone height of 4, which had been wetted with 0.5 g of water.

After an exposure time of 15 minutes, the lock was dried for 2 minutes with a hairdryer. A gold-colored lock was obtained.

The coloration thus obtained was highly resistant to shampooing.

Example 3

Methylheptyl Cyanoacrylate Monomer

The following composition was produced:

| | |
|---|---|
| DC 1501 Fluid | 40 g |
| DC 245 Fluid | 40 g |
| Prestige bronze brown iron oxide/mica nacre, Eckart | 10 g |
| Methylheptyl cyanoacrylate from Chemence | 10 g |

0.5 g of the composition was applied to a lock of 1 g of clean, wet hair. After an exposure time of 15 minutes, the lock was dried with a hairdryer for 2 minutes.

The lock was colored and the coloration obtained was resistant to shampoo.

Example 4

Methylheptyl Cyanoacrylate Monomer with Acetic Acid

The following composition A was produced:

| | |
|---|---|
| Methylheptyl cyanoacrylate from Chemence | 97.5 g |
| Glacial acetic acid | 2.5 g |

The following composition B was produced:

| | |
|---|---|
| DC 1501 Fluid | 40 g |
| DC 245 Fluid | 40 g |
| Prestige bronze nacre, Eckart | 10 g |
| Composition A | 10 g |

0.5 g of composition B was applied to a lock of 1 g of clean, wet hair. After an exposure time of 15 minutes, the lock was dried with a hairdryer for 2 minutes.

The lock was colored and the coloration obtained was resistant to shampoo.

Example 5

Ethylhexyl Cyanoacrylate Monomer

The following composition was produced:

| | |
|---|---|
| DC 1501 Fluid | 40 g |
| DC 245 Fluid | 40 g |
| Prestige bronze nacre, Eckart | 10 g |
| Ethylhexyl cyanoacrylate O-60 from Tong Shen | 10 g |

0.5 g of the composition was applied to a lock of 1 g of clean, wet hair. After an exposure time of 15 minutes, the lock was dried with a hairdryer for 2 minutes.

The lock was colored and the coloration obtained was resistant to shampoo.

Example 6

Butyl Cyanoacrylate Monomer

The following composition I was produced:

| | |
|---|---|
| Butyl cyanoacrylate B-60 from Tong Shen | 90 g |
| Glacial acetic acid | 10 g |

The following composition J was produced:

| | |
|---|---|
| DC 1501 Fluid | 40 g |
| DC 245 Fluid | 40 g |
| Prestige bronze nacre, Eckart | 10 g |
| Composition I | 10 g |

1.5 g of composition J was applied to a lock of 1 g of clean, wet hair. After an exposure time of 15 minutes, the lock was dried with a hairdryer for 2 minutes.

The lock was colored and the coloration obtained was resistant to shampoo.

Example 7

Ethoxyethyl Cyanoacrylate Monomer

The following composition K was produced:

| | |
|---|---|
| DC 1501 Fluid | 37.5 g |
| DC 245 Fluid | 37.5 g |
| Prestige bronze nacre, Eckart | 10 g |
| Glacial acetic acid | 5 g |
| Ethoxyethyl cyanoacrylate EO 460 from Tong Shen | 10 g |

0.5 g of the composition K was applied to a lock of 1 g of clean, wet hair. After an exposure time of 15 minutes, the lock was dried with a hairdryer for 2 minutes.

The lock was colored and the coloration obtained was resistant to shampoo.

Example 8

Mixture of Methylheptyl Cyanoacrylate and Ethylhexyl Cyanoacrylate Monomers

The following composition C was produced:

| | |
|---|---|
| Methylheptyl cyanoacrylate from Chemence | 97.5 g |
| Ethylhexyl cyanoacrylate O-60 from Tong Shen | 2.5 g |

The following composition D was produced:

| | |
|---|---|
| DC 1501 Fluid | 40 g |
| DC 245 Fluid | 40 g |
| Prestige bronze nacre, Eckart | 10 g |
| Composition C | 10 g |

1.5 g of composition D was applied to a lock of 1 g of clean, wet hair. After an exposure time of 15 minutes, the lock was dried with a hairdryer for 2 minutes.

The lock was colored and the coloration obtained was resistant to shampoo.

Example 9

Mixture of Methylheptyl Cyanoacrylate and Butyl Cyanoacrylate Monomers

The following composition E was produced:

| | |
|---|---|
| Methylheptyl cyanoacrylate from Chemence | 67.5 g |
| Butyl cyanoacrylate B-60 from Tong Shen | 27.5 g |
| Glacial acetic acid | 5 g |

The following composition F was produced:

| | |
|---|---|
| DC 1501 Fluid | 40 g |
| DC 245 Fluid | 40 g |
| Prestige bronze nacre, Eckart | 10 g |
| Composition E | 10 g |

1.5 g of composition F was applied to a lock of 1 g of clean, wet hair. After an exposure time of 15 minutes, the lock was dried with a hairdryer for 2 minutes.

The lock was colored and the coloration obtained was resistant to shampoo.

Example 10

Titanium Oxide/Mica Nacre

The following composition was produced:

| | |
|---|---|
| DC 1501 Fluid | 40 g |
| DC 245 Fluid | 40 g |
| Prestige Gold titanium oxide/mica nacre, Eckart | 10 g |
| Methylheptyl cyanoacrylate from Chemence | 10 g |

0.5 g of the composition was applied to a lock of 1 g of clean, wet hair. After an exposure time of 15 minutes, the lock was dried with a hairdryer for 2 minutes.

The lock was colored and the coloration obtained was resistant to shampoo.

Example 11

Iron Oxide-Titanium Oxide/Mica Nacre

The following composition was produced:

| | |
|---|---|
| DC 1501 Fluid | 40 g |
| DC 245 Fluid | 40 g |
| Prestige Sun Gold brown iron oxide-titanium oxide/mica nacre, Eckart | 10 g |
| Methylheptyl cyanoacrylate from Chemence | 10 g |

0.5 g of the composition was applied to a lock of 1 g of clean, wet hair. After an exposure time of 15 minutes, the lock was dried with a hairdryer for 2 minutes.

The lock was colored and the coloration obtained was resistant to shampoo.

Example 12

Iron Oxide/Synthetic Mica Nacre

The following composition was produced:

| | |
|---|---|
| DC 1501 Fluid | 40 g |
| DC 245 Fluid | 40 g |
| Sunshine super bronze brown iron oxide/synthetic mica (fluorophlogopite) nacre from Sun Chemical | 10 g |
| Methylheptyl cyanoacrylate from Chemence | 10 g |

0.5 g of the composition was applied to a lock of 1 g of clean, wet hair. After an exposure time of 15 minutes, the lock was dried with a hairdryer for 2 minutes.

The lock was colored and the coloration obtained was resistant to shampoo.

Example 13

Titanium Oxide/Synthetic Mica Nacre

The following composition was produced:

| | |
|---|---|
| DC 1501 Fluid | 40 g |
| DC 245 Fluid | 40 g |
| Sunshine super blue titanium oxide/synthetic mica (fluorophlogopite) nacre from Sun Chemical | 10 g |
| Methylheptyl cyanoacrylate from Chemence | 10 g |

0.5 g of the composition was applied to a lock of 1 g of clean, wet hair. After an exposure time of 15 minutes, the lock was dried with a hairdryer for 2 minutes.

The lock was colored and the coloration obtained was resistant to shampoo.

Example 14

Titanium Black Pigment

The following composition was produced:

| | |
|---|---|
| DC 1501 Fluid | 40 g |
| DC 245 Fluid | 39.2 g |
| Titanium Black pigment from Biosynthis | 10 g |
| Polyhydroxystearic acid dispersant, sold under the name Octacare DSP OL 300 by Avecia | 0.8 g |
| Methylheptyl cyanoacrylate from Chemence | 10 g |

0.5 g of the composition was applied to a lock of 1 g of clean, wet hair. After an exposure time of 15 minutes, the lock was dried with a hairdryer for 2 minutes.

The lock was colored and the coloration obtained was resistant to shampoo.

Example 15

Black Iron Oxide

The following composition was produced:

| | |
|---|---|
| DC 1501 Fluid | 40 g |
| DC 245 Fluid | 39.2 g |
| Natpure Black LC 9089 black iron oxide from Sensient | 10 g |
| Polyhydroxystearic acid dispersant, sold under the name Octacare DSP OL 300 by Avecia | 0.8 g |
| Methylheptyl cyanoacrylate from Chemence | 10 g |

0.5 g of the composition was applied to a lock of 1 g of clean, wet hair. After an exposure time of 15 minutes, the lock was dried with a hairdryer for 2 minutes.

The lock was colored and the coloration obtained was resistant to shampoo.

Example 16

Fluorescent Pigment

The following composition was produced:

| | |
|---|---|
| DC 1501 Fluid | 40 g |
| DC 245 Fluid | 39.2 g |
| Sunbrite SG2516 Red orange fluorescent pigment from Sun Chemical | 10 g |
| Polyhydroxystearic acid dispersant, sold under the name Octacare DSP OL 300 by Avecia | 0.8 g |
| Methylheptyl cyanoacrylate from Chemence | 10 g |

0.5 g of the composition is applied to a lock of 1 g of clean, wet hair. After an exposure time of 15 minutes, the lock was dried with a hairdryer for 2 minutes.

The lock was colored and the coloration obtained was resistant to shampoo.

Example 17

Quantum Dots

The following composition G was produced:

| | |
|---|---|
| DC 1501 Fluid | 40 g |
| DC 245 Fluid | 40 g |
| Quantum Dots (CdSe—ZnS, emission 603 nm) sold by the company Evident Technologies | 10 g |
| Methylheptyl cyanoacrylate from Chemence | 10 g |

1.5 g of composition G was applied to a lock of 1 g of clean, wet hair. After an exposure time of 15 minutes, the lock was dried with a hairdryer for 2 minutes.

The lock was colored orange and the coloration obtained was resistant to shampoo.

Example 18

Quantum Dots as Pretreatment

The following composition H was produced:

| | |
|---|---|
| Quantum Dots (CdSe—ZnS, emission 603 nm) sold by the company Evident Technologies | 10 g |

The following composition I was produced:

| | |
|---|---|
| DC 1501 Fluid | 45 g |
| DC 245 Fluid | 45 g |
| Methylheptyl cyanoacrylate from Chemence | 10 g |

1 g of composition H was applied to a lock of 1 g of clean, wet hair. The lock was dried and then rewetted. 1 g of composition I was then applied. After an exposure time of 15 minutes, the lock was dried with a hairdryer for 2 minutes.

The lock was colored orange and the coloration obtained was resistant to shampoo.

What is claimed is:

1. A process for dyeing keratin materials comprising applying to the keratin materials a dyeing composition comprising, in a suitable dyeing medium, at least one pigment in an amount greater than 5% by weight relative to the total weight of the composition, and at least one electrophilic cyanoacrylate monomer of formula (I)

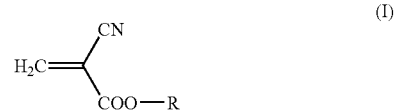

in which R is chosen from alkyl radicals and alkoxyalkyl radicals, wherein the dyeing process results in a shampoo resistant coloration.

2. The process according to claim 1, wherein the at least one electrophilic cyanoacrylate monomer is chosen such that in formula (I), the alkyl radicals or alkoxyalkyl radicals of R comprise from 1 to 10 carbon atoms.

3. The process according to claim 2, wherein in formula (I), the alkyl radicals or alkoxyalkyl radicals of R comprise from 6 to 10 carbon atoms.

4. The process according to claim 3, wherein the at least one electrophilic cyanoacrylate monomer of formula (I) is chosen from alkyl($C_6$-$C_{10}$) cyanoacrylates.

5. The process according to claim 1, wherein the at least one electrophilic cyanoacrylate monomer is an n-octyl 2-cyanoacrylate.

6. The process according to claim 1, wherein the at least one electrophilic cyanoacrylate monomer is present in an amount ranging from 0.1% to 80% by weight, relative to the total weight of the composition.

7. The process according to claim 1, wherein the at least one pigment is in the form of a pigment paste or powder.

8. The process according to claim 7, wherein the at least one pigment is chosen from inorganic pigments chosen from titanium dioxide, with or without surface treatment, oxides of zirconium, oxides of cerium, oxides of iron, oxides of chromium, manganese violet, ultramarine blue, chromium hydrate and Prussian blue.

9. The process according to claim 7, wherein the at least one pigment is chosen from organic pigments chosen from nitroso, nitro, azo, xanthene, quinoline, anthraquinone and phthalocyanine compounds, metal complex compounds, and isoindolinone, isoindoline, quinacridone, perinone, perylene, diketopyrrolopyrrole, thioindigo, dioxazine, triphenylmethane and quinophthalone compounds.

10. The process according to claim 7, wherein the at least one pigment is chosen from composite pigments composed of particles comprising an inorganic core, at least one binder attaching the organic pigments to the core, and at least one organic pigment at least partly covering the core.

11. The process according to claim 7, wherein the at least one pigment is chosen from lakes comprising an inorganic substrate chosen from alumina, silica, calcium sodium borosilicate, calcium aluminium borosilicate, and aluminium, on which a dye is adsorbed.

12. The process according to claim 7, wherein the at least one pigment is chosen from special-effect pigments chosen from nacreous pigments, interference-effect pigments not attached to a substrate, fluorescent pigments, phosphorescent pigments, photochromic pigments, thermochromic pigments and quantum dots.

13. The process according to claim 12, wherein the at least one nacreous pigment is chosen from mica coated with titanium, mica coated with bismuth oxychloride, mica coated with titanium and iron oxides, mica coated with titanium and Prussian blue or chromium oxide, nacreous pigments based on bismuth oxychloride, and mica coated with titanium and at least one organic pigment chosen from nitroso, nitro, azo, xanthene, quinoline, anthraquinone and phthalocyanine compounds, metal complex compounds, and isoindolinone, isoindoline, quinacridone, perinone, perylene, diketopyrrolopyrrole, thioindigo, dioxazine, triphenylmethane and quinophthalone compounds.

14. The process according to claim 11, wherein the at least one interference-effect pigment not attached to a substrate is chosen from liquid crystals and holographic interference flakes.

15. The process according to claim 1, wherein the at least one pigment is chosen from colored pigments.

16. The process according to claim 1, wherein the at least one pigment is present in the composition, in an amount ranging from greater than 5% up to and including 50% by weight, relative to the total weight of the composition.

17. The process according to claim 16, wherein the at least one pigment is present in the composition, in an amount ranging from greater than 5% up to and including 35% by weight, relative to the total weight of the composition.

18. The process according to claim 1, wherein the size of the at least one pigment ranges from 10 nm to 200 μm.

19. The process according to claim 1, wherein the composition is anhydrous.

20. The process according to claim 1, wherein the suitable dyeing medium is chosen from aromatic alcohols, fatty alcohols, modified or non-modified polyols, volatile or non-volatile silicones, mineral oils, organic oils or vegetable oils, oxyethylenated or nonoxyethylenated waxes, paraffins, alkanes, fatty acids, fatty amides and fatty esters.

21. The process according to claim 1, wherein the composition further comprises at least one nucleophile.

22. The process according to claim 21, wherein the at least one nucleophile is water.

23. The process according to claim 21, wherein
at least one first composition comprising the at least one pigment is applied to the keratin materials, and
at least one second composition comprising the at least one electrophilic cyanoacrylate monomer of formula (I), is applied to the keratin materials, wherein the at least one nucleophile is present in the at least one first composition comprising the pigment, or in a separate third composition.

24. The process according to claim 23, wherein the at least one first composition comprising the at least one pigment is an aqueous pigment composition and the at least one second composition comprising the at least one electrophilic cyanoacrylate monomer of formula (I) is anhydrous.

25. The process according to claim 1, wherein the keratin materials are keratin fibers.

26. A coloring kit comprising
at least one first composition comprising at least one pigment,
at least one second composition comprising at least one electrophilic cyanoacrylate monomer of formula (I):

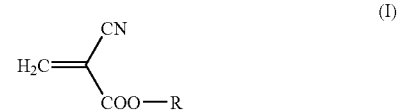

in which R is chosen from alkyl radicals and alkoxyalkyl radicals, and
at least one third composition comprising at least one nucleophile,
wherein the at least one pigment is present in an amount greater than 5% by weight relative to the total weight of the at least one first composition combined with the at least one second composition, and
wherein the resultant coloration from the coloring kit is shampoo resistant.

27. The coloring kit according to claim 26, wherein the at least one first composition comprising the at least one pigment and the at least one second composition comprising the at least electrophilic cyanoacrylate monomer of formula (I) are present in the same anhydrous composition.

28. A dyeing composition comprising, in a suitable dyeing medium,
at least one pigment in an amount greater than 5% by weight relative to the total weight of the composition, and
at least one electrophilic cyanoacrylate monomer of formula (I):

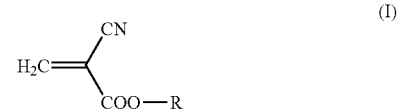

in which R is chosen from alkyl radicals and alkoxyalkyl radicals,
wherein the dyeing composition results in a shampoo resistant coloration.

* * * * *